US011110597B2

(12) United States Patent
Polygerinos et al.

(10) Patent No.: US 11,110,597 B2
(45) Date of Patent: Sep. 7, 2021

(54) SOFT POLY-LIMB SYSTEMS

(71) Applicants: Panagiotis Polygerinos, Gilbert, AZ (US); Pham Huy Nguyen, Mesa, AZ (US)

(72) Inventors: Panagiotis Polygerinos, Gilbert, AZ (US); Pham Huy Nguyen, Mesa, AZ (US)

(73) Assignee: Arizona Board of Regents on behalf of Arizona State University, Scottsdale, AZ (US)

(*) Notice: Subject to any disclaimer, the term of this patent is extended or adjusted under 35 U.S.C. 154(b) by 35 days.

(21) Appl. No.: 16/381,637

(22) Filed: Apr. 11, 2019

(65) Prior Publication Data
US 2019/0314980 A1    Oct. 17, 2019

Related U.S. Application Data

(60) Provisional application No. 62/656,481, filed on Apr. 12, 2018, provisional application No. 62/776,770, filed on Dec. 7, 2018.

(51) Int. Cl.
| | | |
|---|---|---|
| *B25J 9/06* | (2006.01) | |
| *A61F 2/54* | (2006.01) | |
| *B25J 9/16* | (2006.01) | |
| *B25J 9/00* | (2006.01) | |
| *B25J 9/14* | (2006.01) | |
| *B25J 13/02* | (2006.01) | |

(52) U.S. Cl.
CPC ................................ *B25J 9/06* (2013.01); *A61F 2/54* (2013.01); *B25J 9/0006* (2013.01); *B25J 9/142* (2013.01); *B25J 9/1612* (2013.01); *B25J 9/1694* (2013.01); *B25J 13/02* (2013.01)

(58) Field of Classification Search
CPC .... B25J 9/065; B25J 9/14–148; B25J 9/1612; B25J 9/1694; B25J 9/0006; B25J 13/02; G05B 2219/40305; A61F 2/54
See application file for complete search history.

(56) References Cited

U.S. PATENT DOCUMENTS 4,784,042 A  *  11/1988  Paynter ................... B25J 9/142
                                                           414/7
4,792,173 A  *  12/1988  Wilson .................. B25J 9/1075
                                                           294/119.3
(Continued)

FOREIGN PATENT DOCUMENTS

WO     WO2019183397 A1    9/2019

OTHER PUBLICATIONS

Fraction et al., Invincible Iron Man (2008) # 502, Mar. 16, 2011, Marvel, Issue # 502. (Year: 2021).*
(Continued)

*Primary Examiner* — Daniel D Yabut
(74) *Attorney, Agent, or Firm* — Snell & Wilmer L.L.P.

(57) ABSTRACT

The present disclosure provides a soft poly-limb system, comprising a first actuator segment, a second actuator segment, and a third actuator segment forming the soft poly-limb. Each of the first actuator segment, the second actuator segment, and the third actuator segment may comprise a plurality of ring reinforced actuators. The soft poly-limb system may further comprise a control system whereby a user may control the soft poly-limb.

12 Claims, 8 Drawing Sheets

(56) References Cited

U.S. PATENT DOCUMENTS

| | | | | |
|---|---|---|---|---|
| 6,689,074 | B2* | 2/2004 | Seto | A61F 2/54 |
| | | | | 601/33 |
| 6,718,766 | B2* | 4/2004 | Seto | B25J 9/142 |
| | | | | 60/476 |
| 8,201,473 | B2* | 6/2012 | Knoll | A61B 1/00156 |
| | | | | 74/490.05 |
| 8,863,608 | B2* | 10/2014 | Fischer | B25J 18/06 |
| | | | | 74/490.04 |
| 9,393,173 | B1* | 7/2016 | Meza | A61H 3/04 |
| 2010/0258362 | A1* | 10/2010 | Trimmer | B08B 9/045 |
| | | | | 180/7.1 |
| 2014/0109560 | A1* | 4/2014 | Ilievski | B25J 9/142 |
| | | | | 60/327 |
| 2015/0001269 | A1* | 1/2015 | Sacksteder | B25J 19/002 |
| | | | | 224/576 |
| 2015/0070904 | A1* | 3/2015 | Martinez | F21V 17/02 |
| | | | | 362/320 |
| 2015/0217444 | A1* | 8/2015 | Asada | B25J 9/0006 |
| | | | | 700/258 |
| 2015/0240958 | A1* | 8/2015 | Mosadegh | F16K 11/20 |
| | | | | 137/12 |
| 2016/0263751 | A1* | 9/2016 | Galloway | B25J 18/06 |
| 2017/0259427 | A1* | 9/2017 | Asada | B25J 9/0006 |
| 2017/0291806 | A1* | 10/2017 | Lessing | B25J 9/1612 |
| 2018/0289522 | A1 | 10/2018 | Zhu et al. | |
| 2018/0338807 | A1* | 11/2018 | Kim | B25J 9/142 |
| 2019/0029914 | A1 | 1/2019 | Polygerinos et al. | |
| 2019/0167504 | A1 | 6/2019 | Polygerinos et al. | |
| 2019/0247217 | A1 | 8/2019 | Govin et al. | |
| 2019/0336315 | A1 | 11/2019 | Polygerinos et al. | |
| 2019/0374422 | A1* | 12/2019 | Yeow | F15B 15/103 |

OTHER PUBLICATIONS

Kirby, R. S. et al. Prevalence and functioning of children with cerebral palsy in four areas of the United States in 2006: A report from the Autism and Developmental Disabilities Monitoring Network. Res. Dev. Disabil. 32, 462-469 (2011).
Lubelski, D. et al. Correlation of quality of life and functional outcome measures for cervical spondylotic myelophathy. J. Neurosurg. Spine 24, 483-489 (2016).
Ajiboye, A.B. et al. Articles Restoration of researching and grasping movements through brain-controlled muscle stimulation in a person with tetraplegia : a proof-of-concept-demonstration. Lancet 6736, 1-10 (2017).
Bogue, R. Exoskeletons and robotic prosthetics: a review of recent developments. Ind. Robot an Int. J. 36, 421-427 (2009).
Gopura, R. A. R. C., Kiguchi, K. & Bandara, D.S.V. A brief review on upper extremity robotic exoskeleton systems a Brief Review on Upper Extremity Robotic Exoskeleton Systems. 8502, 346-251 (2015).
Parietti, F. & Asada, H.H. Supernumerary Robotic Limbs for aircraft fuselage assembly: Body stabilization and guidance by bracing. Proc.—IEEE Int. Conf. Robot. Autom. 1176-1183 (2014). doi: 10.1109/ICRA.2014.6907002.
Kurek, D.A. & Asada. H.H. The MantisBot: Design and Impedance of Control of Supernumerary Robotic Limbs for Near-Ground Work. 5942-5947 (2017).
Parietti, F., Chang, K. C., Hunter, B. & Asada. H.H. Design and control of Supernumerary Robotic Limbs for balance augmentation. Robot. Autom. (ICRA), 2015 IEEE Int. Conf. 5010-5017 (2015). doi: 10.1109/ICRA.2015.7139896.
Qureshi, A. H., Nakamura, Y., Yoshikawa, Y. & Ishiguro, H. Show, Attend and Interact: Perceivable Human-Robot Social Interaction through Neural Attention Q-Network. 1639-1645 (2017).
Wu, F.Y. & Asada, H.H. 'Hold-and-manipulate' with a single hand being assisted by wearable extra fingers. Proc.—IEEE Int. Conf. Robot. Autom. Jun. 2015, 6205-6212 (2015).
Wu, F. Y. & Asada, H.H. Implicit and Intuitive Grasp Posture Control for Wearable Robotic Fingers: A Data-Driven Method Using Partial Least Squares. IEEE Trans. Robot. 32, 176-186 (2016).

Tiziani, L et al. Empirical characterization of modular variable stiffness inflatable structures for supernumerary grasp-assist devices. 1-23 (2017). doi: 10.1177/0278364917714062.
Guterstam, A., Petkova, V.I. & Ehrsson, H.H. The Illusion of Owning a Third Arm. 6, (2011).
Tsakiris, M. & Carpenter, L. Hands only illusion: multisensory integration elicits sense of ownership for body parts but not for non-corporeal objects. 343-352 (2010). doi: 10.1007/s00221-009-2039-3.
Parietti, F. & Asada, H. H. Independent, Voluntary Control of Extra Robotic Limbs. 5954-5961 (2017).
Sasaki, T., Saraiji, M. Y., Fernando, C.L. Minamizawa, K. & Inami, M. MetaLimbs. ACS SIGGRAPH 2017 Posters—SIGGRAPH '17 1, 1-2 (2017).
Sada, M. AI, Khamis, M. & Kato, A. Challenges and Opportunities of Supernumerary Robotic Limbs. (2017).
Del-Alma, A.J. et al. Review of hybrid exoskeletons to restore gait following spinal cord injury. J. Rehabil. Res. Dev. 49, 497 (2012).
Polygerinos, P. et al. Soft Robotics: Review of Fluid-Driven Intrinsically Soft Devices; Manufacturing, Sensing, Control, and Applications in Human-Robot Interaction. Adv. Eng. Mater. e201700016—n/a doi:10.1002/adem.201700016.
Simpson, C.S., Okamura, A.M. & Hawkes, E.W. Exomuscle: An inflatable device for shoulder abduction support. 6651-6657 (2017).
Awad, L.N. et al. A soft robotic exosuit improves walking after stroke. Sci. Transl. Med. in Press, (2017).
Polygerinos, P. et al. Towards a soft pneumatic glove for hand rehabilitation. IEEE Int. Conf. Intel. Robot. Syst. 1512-1517 (2013). doi10.1109/IROS.2013.6696549.
Polygerinos, P. et al. Modeling of soft Fiber-Reinforced Bending Actuators. IEEE Trans. Robot. 31, 778-789.
Klute, G.K. Czerniercki, J.M. & Hannaford, B. McKibben Artificial Muscles: Pneumatic Actuators with Biomedical Intelligence. 1-6 (1999).
Niiyama, R., Rus, D. & Kim, S. Pouch Motors : Printable / Inflatable Soft Actuators for Robotics. 6332-6337 (2014).
McMahan, W., Jones , B.A. & Walker, I.D. Design and implementation of a multi-section continuum robot: Air-octor. 2005 IEEE/RSJ Int. Conf. Intell. Robot. Syst. IROS 3345-3352 (2005). doi: 10.1109/IROS.2005.1545487.
Calisti, M. et al. An octopus-bioinspired solution to movement and manipulation for soft robots. Bioinspir. Biomim. 6, 36002 (2011).
Walker, I.D. et al. Continuum robot arms inspired by cephalopods. SPIE Conf. Unmanned Gr. Veh. Techol. 5804, 303-314 (2005).
Godage, I.S., Medrano-Cerda, G.A., Branson, D.T., Guglielmino, E. & Caldwell, D.G. Dynamics for variable length multisection continium arms. Int. J. Rob. Res. 35, 695-722 (2016).
Ansari, Y. et al. Towards the development of a soft manipulator as an assistive robot for personal care of elderly people. Int. J. Adv. Robot. Syst. 14, 1-17 (2017).
Sanan, S. Soft Inflatable Robots for Safe Physical Human Interaction. Carnegie Mellon Univ. 3575511, 240 (2013).
Hawkes, E. W., Blumensch, L.H., Greer, J.D. & Okamura, A.M.A. soft robot that navigated its environment through growth. 1-8 (2017).
Best, B.C.M. et al. A New Soft Robot Control Method. 75-84 (2016).
Cianchetti, M. et al. STIFF-FLOP Surgical Manipulator: mechanical design an experimental characterizations of the single module. 3576-3581 (2013).
Marchese, A.D. & Rus, D. Design, kinematics, and control of a soft spatial fluidic elastomer manipulator. Int. J. Rob. Res. 02783649155587925.
Nguyen, P.H., Sridar, S., Zhang, W. & Polygerinos, P. Design and Control of a 3-Chambered Fiber Reinforced Soft Actuator with Off-the-shelf Stretch Senors. Int. J. Intell. Robot. Appl. to appear, (2017).
Plagenhoef, S., Evans F.G. & Abdelnour, T. anatomical Data for Analyzing Human Motion. Res. Q. Exerc. Sport 54,169-178 (1983).
Kier, W.M. & Smith, K.K. The biomechanics of movement in tongues and tentacles. J. Biomech. 16, 292-293 (1983).

(56) References Cited

OTHER PUBLICATIONS

Charles, J.P., Cappellari, O., Spence, A.J., Hutchinson, J.R. & Wells, D.J. Musculoskeletal geometry, muscle architecture and functional specialisations of the mouse hindlimb. PLoS One 11, 1-21 (2016).
Connolly, F., Walsh, C.J. & Bertoldi, K. Automatic design of fiber-reinforced soft actuators for trajectory matching. Proc. Natl. Acad. Sci. 201615140 (2016). doi: 10.1073/pnas.1615140114.
Bishnop-Moser, J. & Kota, S. Design and Modeling of Generalized Fiber-Reinforced Pneumatic Soft Actuators. IEEE Trans. Robot. 31, 536-546 (2015).
Deimel, R. & Brock, O. A complaint hand based on a novel pneumatic actuator. Proc.—IEEE Int. Conf. Robot. Autom. 2047-20533 (2013). doi:10.1109/ICRA.2013.6630851.
Agarwal, G., Besuchnet, N., Audergon, B. & Paik, J. Stretchable Materials for Robust Soft Actuators towards Assistive Wearable Devices. Nat. Publ. Gr. 1-8 (2016). doi:10.1038.srep34224.
Connolly, F., Polygerinos, P., Walsh, C.J. & Bertoldi, K. Mechanical Programming of Soft Actuators by Varying Fiber Angle. Soft Robot. 2, 26-32 (2015).
Yeoh, O.H. Some Forms of the Strain Energy Function for Rubber. Rubber Chemistry and Technolgy 66, 754-771 (1993).
Maria Elena Giannaccini, Chaoqun Xiang, Adham Atyabi, Theo Theodoridis, Samia Nefti-Meziani, Steve Davis, Giannaccini Maria Elena, Xiang Chaoqun, Atyabi Adham, Theodoridis Theo, Nefti-Meziani Samia, and Davis Steve. Novel Design of a Soft Lightweight Pneumatic Continuum Robot Arm with Decoupled Variable Stiffness and Positioning. Soft Robotics, 00(00):soro.2016.0066, 2017.
Moseley, P. et al. Modeling, Design, and Development of Soft Pneumatic Actuators with Finite Element Method. Adv. Eng. Mater. 18, 978-988 (2016).
Vighnesh Vatsal and Guy Hoffman. Wearing Your Arm on Your Sleeve: Studying Usage Contexts for a Wearable Robotic Forearm. In 2017 IEEE International Symposium on Robot and Human Interactive Communication (RO-MAN), pp. 974-980, Aug. 2017.
Irfan Hussain, Gionata Salvietti, Giovanni Spanoletti, Monica Malvezzi, David Cioncoloni, Simone Rossi, and Domenico Prattichizzo. A soft supernumerary robotic finger and mobile arm support for graping compensation and hemiparetic upper limb rehabilitation. Robotics and Autonomous Systems, 93:1-12, 2017.
Matthew A Robertson and Jamie Paik. New soft robots really suck: Vacuum-powered systems empower diverse capabilities. Science Robotics, 2(9):1-12, 2017.
Zheyuan Gong, Jiahui Cheng, Xingyu Chen, Wenguang Sun, Xi Fang, and Kainan Hu. A Bio-inspired Soft Robotic Arm : Kinematic Modeling and Hydrodynamic Experiments. Journal of Bionic Engineering, 15:204-219, 2018.
Junius Santoso, Erik H Skorina, Ming Luo, Ruibo Yan, and Cagdas D Onal. Design and analysis of an origami continuum manipulation module with torsional strength. In IEEE International Conference on Intelligent Robots and Systems, vol. Sep. 2017, pp. 2098-2104, 2017.
Ohta Preston, Valle Luis, King Jonathan, Low Kevin, Yi Jaehyun, Atkeson Christopher G., Park Yong-Lae, Preston Ohta, Luis Valle, Johnathan King, Kevin Low, Jaehyun Yi, Christopher G. Atkeson, and Yong-Lae Park. Design of a Lightweight Soft Robotic Arm Using Pneumatic Artificial Muscles and Inflatable Sleeves. Soft Robotics, 0(0): null, 2017.
Xianquan Liang, Haris Cheong, Yi Sun, Jin Guo, Chee Kong Chui, and C Yeow. Design, Characterizations and Implementation of a Two—DOF Fabric—basd Soft Robotic Arm. IEEE Robotics and Automation Letters, 3766(c):1-8, Jul. 2018.
Masashi Takeichi, Koichi Suzumori, Gen Endo, and Hiroyuki Nabae. Development of Giacometti Arm With Ballon Body. IEEE Robotics and Automation Letters, 2(2):2710-2716, 2017.
Hye Jong Kim, Akihiro Kawamura, Yasutaka Nishioka, and Sadao Kawamura. Mechanical design and control of inflatable robotic arms for high positioning accuracy. Advanced Robotics, 32(2):89-104, 108.
Xianquan Liang, Hong Kai Yap, J Guo, R C H Yeow, Y Sun, and C K Chui. Design and characterizations of a novel fabric-based robotic arm for future wearable robot application. In 2017 IEEE International Conference on Robotics and Biomimetrics (ROBIO), pp. 367-372, Dec. 2017.
Pham Huy Nguyen, Curtis Sparks, Sai Gautham Nuthi, Nicholas M Vale, and Panagiotis Polygerinos. Soft Poly-Limbs: Towards a New Paradigm of Mobile Manipulation for Daily Living Tasks. Soft Robotics, 00(00):soro.2018.0065, 2018.
Carly M. Thalman, Quoc P. Lam, Pham H. Nguyen, Saivimal Sridar, and Panagiotis Polygerinos. a Novel Soft Elbow Exosuit to Supplement Bicep Lifting Capacity. In 2018 IEEE/RSJ International Conference on Intelligent Robots and Systems, IROS, 2018. [Accepted].
W. Zhang and P Polygerinos. Distributed planning of multi-segment soft robotic arms. In 2018 Annual American Control Conference (ACC), pp. 2096-2101, Jun. 2018.

* cited by examiner

SOFT POLY-LIMB SYSTEMS

CROSS-REFERENCE TO RELATED APPLICATIONS

This application claims priority to and the benefit of U.S. Provisional Patent Application Ser. No. 62/656,481, entitled "SOFT POLY-LIMB SYSTEMS," filed Apr. 12, 2018, and U.S. Provisional Patent Application Ser. No. 62/776,770, entitled "SOFT ROBOTIC LIMB," filed Dec. 7, 2018. The disclosures of all the foregoing applications are incorporated herein by reference in their entireties, including but not limited to those portions that specifically appear hereinafter, but except for any subject matter disclaimers or disavowals, and except to the extent that the incorporated material is inconsistent with the express disclosure herein, in which case the language in this disclosure shall control.

FEDERALLY SPONSORED RESEARCH OR DEVELOPMENT

This invention was made with government support under grant number CMMI-1800940 awarded by the National Science Foundation. The Government has certain rights in the invention.

TECHNICAL FIELD

The present disclosure relates to robotics, and in particular to soft robotic limb systems suitable for supplementing human limbs and, more generally, for moving and manipulating objects.

BACKGROUND

Robotic appendages have been developed which may assist a human user in conducting routine tasks such as moving and manipulating objects. Typically, such robotic appendages are not designed to replace biological limbs, but instead, supplement them. Traditional robotic appendages, for example robotic arms, have suffered from various drawbacks and limitations due to rigid designs, excessive weight and size, and difficult interactions between the robotic appendage and human tissue. Accordingly, improved robotic appendages remain desirable.

BRIEF DESCRIPTION OF THE DRAWINGS

With reference to the following description and accompanying drawings.

SUMMARY

In an exemplary embodiment, a soft poly-limb system may comprise a first actuator segment, a second actuator segment, and a third actuator segment forming the soft poly-limb, wherein each of the first actuator segment, the second actuator segment, and the third actuator segment comprise a plurality of ring reinforced actuators, and a control system whereby a user may control the soft poly-limb.

In various embodiments, each ring reinforced actuator may be fluid-driven and comprise a plurality of rings dispersed along an external surface of an actuator body. The plurality of rings may be configured to restrain radial expansion and promote linear extension motion. The soft poly-limb may be configured with nine degrees of freedom. The soft poly-limb may have a length of between 0.5 meters and 0.7 meters. Each actuator segment may be tapered such that the soft poly-limb may be tapered. Each ring reinforced actuator may have a first diameter at one end and a second, smaller diameter at a second, opposite end. The system may be wearable by a user to provide enhanced object manipulation capabilities to the user. The system may further comprise an end-effector coupled to the third actuator segment. The system may comprise at least five actuator segments, or at least seven actuator segments, or at least ten actuator segments.

A system may comprise a soft poly-limb, comprising, a first actuator segment, a second actuator segment, and a third actuator segment forming a soft poly-limb, wherein each of the first actuator segment, the second actuator segment, and the third actuator segment may comprise a plurality of ring reinforced actuators, and a motion controller in communication with the soft poly-limb and configured to provide movement instructions to the soft poly-limb.

In various embodiments, the motion controller may comprise one of a joystick motion controller, an inertial measurement unit motion (IMU) controller, or a surface electromyography (sEMG) motion controller. The system may further comprise a pressure source in fluid communication with the soft poly-limb and configured to provide fluid pressure to the soft poly-limb. The system may further comprise a pressure regulator between the pressure source and the soft poly-limb and configured to regulate a pressure of fluid flowing into the soft poly-limb. The system may further comprise a pressure sensor coupled to the soft poly-limb and configured to monitor a pressure in a portion of the soft poly-limb. The system may further comprise a solenoid valve between the pressure regulator and the soft poly-limb.

In an exemplary embodiment, a method of manufacturing a soft poly-limb may comprise forming an actuator body from a first mold, coupling one or more rings to the actuator body to form a ring reinforced actuator, arranging a plurality of ring reinforced actuators in a second mold, forming an actuator segment from the second mold, and coupling a plurality of actuator segments to form the soft poly-limb.

In various embodiments, coupling a plurality of actuator segments may comprise coupling the plurality of actuator segments together via at least one modular connector cap. The first mold may comprise at least one frame segment, a core, and a first cap. Arranging the plurality of ring reinforced actuators may comprise arranging the plurality of ring reinforced actuators in an equilateral triangle prism.

The foregoing features and elements may be combined in various combinations without exclusivity, unless expressly indicated otherwise. These features and elements as well as the operation thereof will become apparent in light of the following description and the accompanying drawings. It should be understood, however, the following description and drawings are intended to be exemplary in nature and non-limiting.

DETAILED DESCRIPTION

The following description is of various exemplary embodiments only, and is not intended to limit the scope, applicability or configuration of the present disclosure in any way. Rather, the following description is intended to provide a convenient illustration for implementing various embodiments including the best mode. As will become apparent, various changes may be made in the function and arrangement of the elements described in these embodiments without departing from principles of the present disclosure.

For the sake of brevity, conventional techniques for robotics, including actuators, joints, power, control, and/or the like may not be described in detail herein. Furthermore, the connecting lines shown in various figures contained herein are intended to represent exemplary functional relationships and/or physical couplings between various elements. It should be noted that many alternative or additional functional relationships or physical connections may be present in a soft poly-limb system and/or components thereof.

Principles of the present disclosure contemplate the use of soft wearable robotics such as soft poly-limbs, for example, for supplementing the capabilities of a human wearer such as in connection with physical assistance of daily living tasks. The present disclosure encompasses the design and development of the fluid-driven, wearable, soft poly-limb, from the Greek word polys, meaning many. The soft poly-limb utilizes the numerous traits of soft robotics to enable a novel approach in providing safe and compliant mobile manipulation assistance to healthy and impaired users. This wearable system equips the user with a controllable additional limb that is capable of complex three-dimensional motion in space. Similar to an elephant trunk, the soft poly-limb is able to manipulate objects using a variety of end-effectors, such as suction adhesion or a soft grasper, as will be discussed further below, as well as its entire soft body to conform around an object. To develop these highly articulated soft robotic limbs, the present disclosure provides a set of systematic design rules, obtained through varying geometrical parameters of the soft poly-limb via experimentally verified finite-element method (FEM) models. Performance of exemplary systems are disclosed by testing the lifetime of the new soft poly-limb actuators, evaluating payload capacity, operational workspace, and capability of interacting close to a user via a spatial mobility test. Further, the present disclosure demonstrates user control of the limb using multiple user intent detection modalities. Exemplary soft poly-limb systems feature the ability to assist in multitasking and pick and place scenarios with varying mounting locations of the soft poly-limb around the user's body. Exemplary embodiments highlight the soft poly-limb's ability to safely interact with the user while demonstrating promising performance in assisting with a wide variety of tasks, in both work and general living settings.

Robotic manipulators that can be worn on the human body provide users with extra appendages to support, assist, or enhance their existing capabilities. Such wearable manipulators do not aim at replacing biological limbs like prosthetic devices or provide musculoskeletal augmentation like exoskeletons. Kinematically, these robots do not have to follow the user's anatomy and therefore do not restrict movement or require alignment with biological joints, and are easier to don and doff. Examples of prior wearable manipulators have ranged from robotic arms, legs, and fingers, showing functional benefits in industrial and medical tasks.

However, the introduction of wearable manipulators brings up the question of adoption and controllability. Previous research has shown that the human central nervous system is capable of accepting and learning to control additional limbs. Therefore, with some training, humans should be capable of working with additional limbs to complete tasks more effectively. Preliminary research has shown controllability of robotic manipulators with multiple human participants, utilizing biological signals from the frontalis muscle on the forehead, torso muscles, the foot, or the elbow. Nevertheless, adoption of such devices goes beyond just being able to control them. There are psychological and social factors involved, for example the stigma of having additional limbs as seen with people with Polymelia (people or animals with more than usual number of biological limbs). A need for a comfortable, easy to don and doff, and lightweight robotic limbs remains.

Although the benefits from the use of wearable manipulators are slowly becoming more apparent, most of the current robotic systems still have to face the obstacles that come with their rigid design, such as weight, size, and the challenging interaction between human tissue and rigid materials. Specifically, prior approaches for wearable robotics, for example robotic arms, legs, and fingers, typically involve the use of pneumatically driven actuators with rigid metal components that add bulk and weight to the design. These challenges lead to questions related to the safety of the user that could possibly limit technological, and later social, adoption. One of the emerging solutions to tackle these challenges originates from soft robotics. Soft robots, or intrinsically soft devices (ISDs), are highly adaptable and robust to the changing environment, safe for human-robot interaction, low-cost in terms of fabrication, lightweight, and finally may offer high power to weight ratios. Their compliant nature allows conformity to the user's body without causing tissue damage, making them suitable for wearable applications. This versatility can promote psychological acceptance of such devices by eliminating some of the constraints of rigidity. This wave of soft robotics has led to the introduction of soft actuators and the possibilities of combining them to create soft continuum manipulators in various categories like cable-driven actuators, pneumatic artificial muscles (PAMs) a.k.a. McKibben actuators, inflatable structures, and fluidic elastomeric actuators (FEAs), The blend of soft robotics and wearable manipulators sets forth a new category of robots, which are referred to herein as soft poly-limbs, i.e. soft manipulators that act as extra appendages.

In accordance with an exemplary embodiment, principles of use of a soft poly-limb may safely and effectively assist a user in numerous ways, such as in activities of daily living (ADLs). In exemplary embodiments, a soft poly-limb as disclosed herein may assist a user by providing daily living assistance (for example, opening a door when a user's hands are full from carrying objects), impaired user assistance (for example, assisting an aging user with feeding), workforce assistance (for example, assisting a grocery store worker user in restacking shelves with products quicker and having access to higher shelves that cannot be reached without the assistance of a soft poly-limb), and/or hazardous task assistance (for example, assisting a user in measuring, from a safe distance, radiation levels emitted from radioactive samples and collecting such radioactive samples on-site). Such forms of assistance are exemplary and not intended to provide all types of assistance the soft poly-limb disclosed herein may offer.

Figure 1:
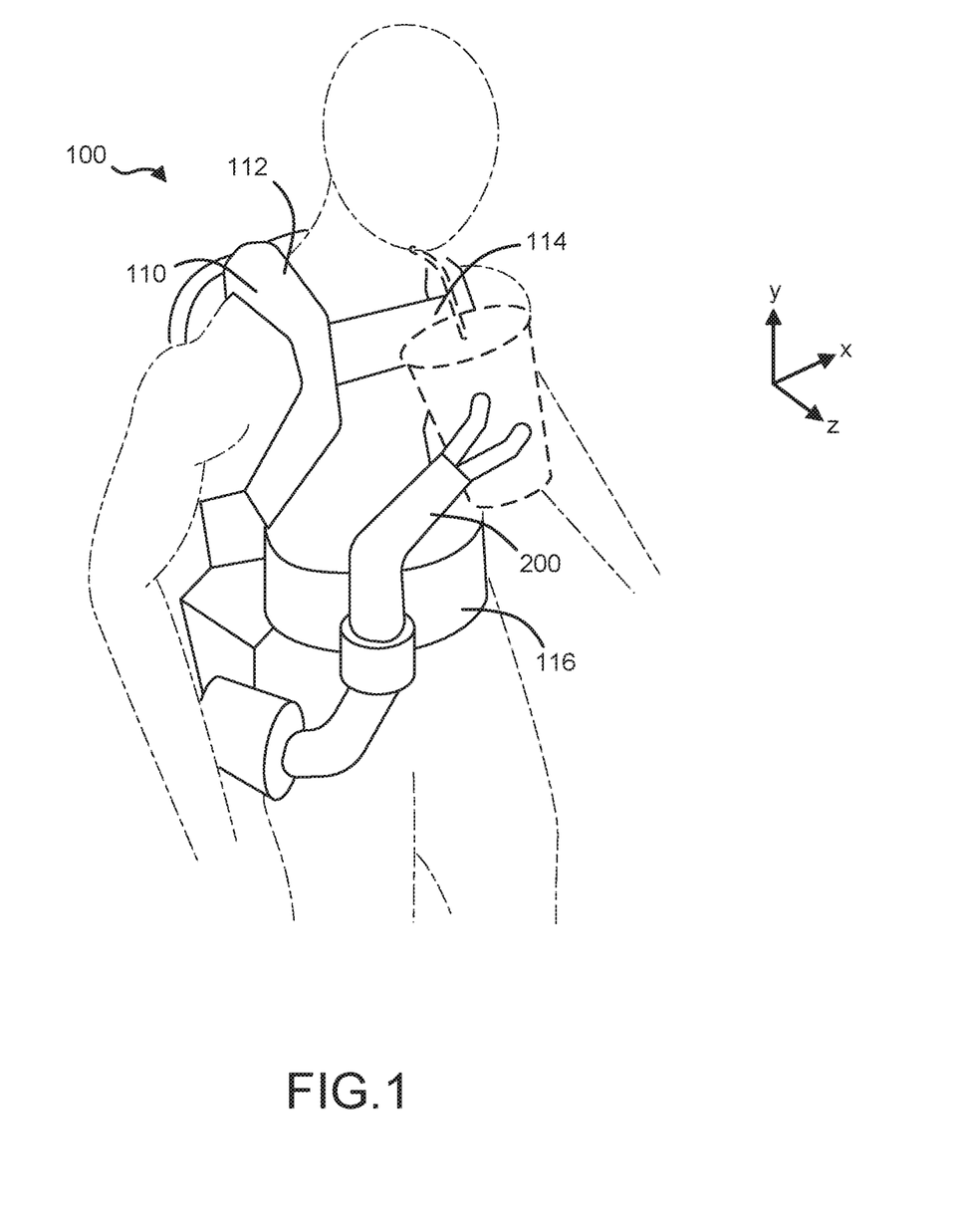
FIG. 1 illustrates a front perspective view of a soft poly-limb system in accordance with an exemplary embodiment.

With reference now to FIG. 1, a soft poly-limb system 100 is illustrated from a front perspective view in accordance with an exemplary embodiment. Soft poly-limb system 100 may comprise a system capable of being worn by a user and having one or more soft poly-limbs 200 configured to assist a user in various tasks including moving, manipulating, maneuvering, and adjusting objects. Soft poly-limb system 100 may comprise a backpack mount 110. In various embodiments, backpack mount 110 may comprise one or more shoulder straps 112, a chest strap 114, and a waist strap 116. In various embodiments, shoulder straps 112, chest strap 114, and waist strap 116 may be coupled together, along with soft poly-limb 200, to form soft poly-limb system 100. Backpack mount 110 may comprise any suitable material capable of supporting and stabilizing soft-poly limb 200, for example a fabric such as a cotton, nylon, polyester, polypropylene, or other suitable fabric.

Figure 2:
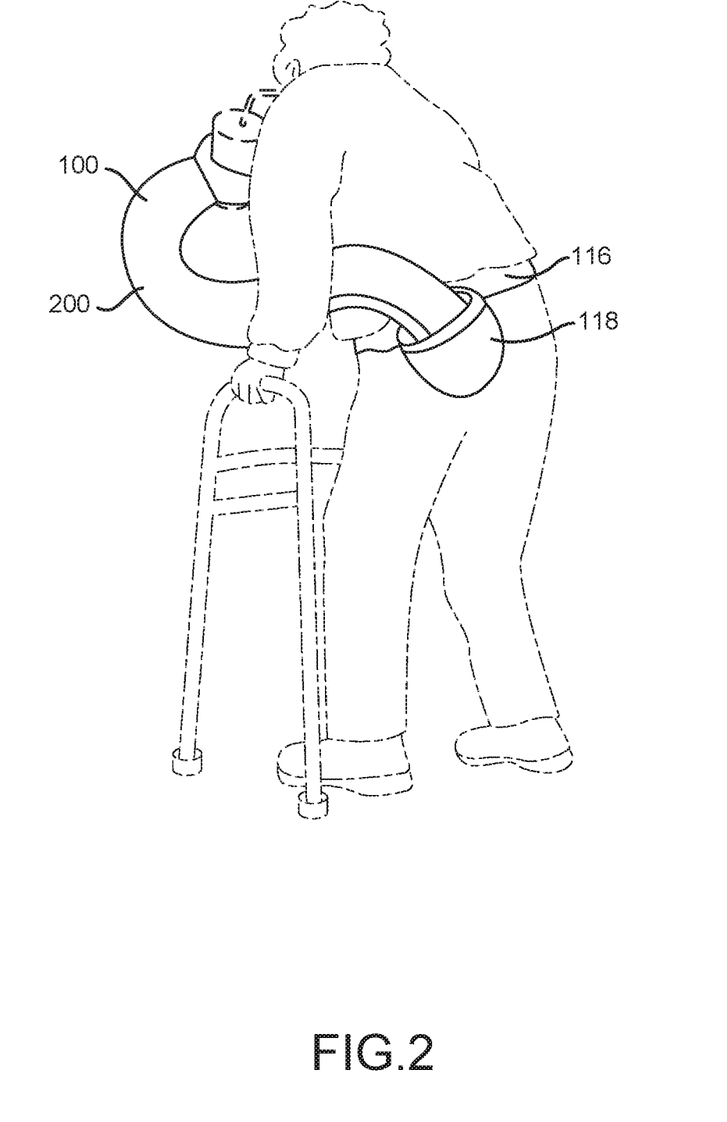
FIG. 2 illustrates a rear perspective view of a soft poly-limb system in accordance with an exemplary embodiment.

Referring now to FIG. 2, soft poly-limb system 100 is illustrated coupled to a user from a rear perspective view in accordance with an exemplary embodiment, Soft poly-limb system 100 may comprise a storage pouch 118 configured to store soft poly-limb 200 when soft poly-limb 200 is not in use or in a collapsed state. Storage pouch 118 may be coupled to waist strap 116, for example, by an outer surface and coupled to soft poly-limb 200 by an outer surface. Soft poly-limb 200 comprising a flexible material (as will be discussed further below), may be configured to collapse, thereby reducing a volume of soft poly-limb 200 and storing soft poly-limb 200 in storage pouch 118. In various embodiments, soft poly-limb 200 may be coupled to storage pouch 118 at a proximal end of the soft poly-limb 200. Storage pouch 118 may comprise a closing mechanism such as a plurality of buttons or fasteners, hook and loop fasteners, or a zipper configured to prevent soft poly-limb 200 from protruding from storage pouch 118 when not in use. While discussed herein as comprising a pouch, storage pouch 118 is not limited in this regard and may comprise any structure capable of storing soft poly-limb 200 in a compact manner when soft poly-limb 200 is not in use.

Figure 3:
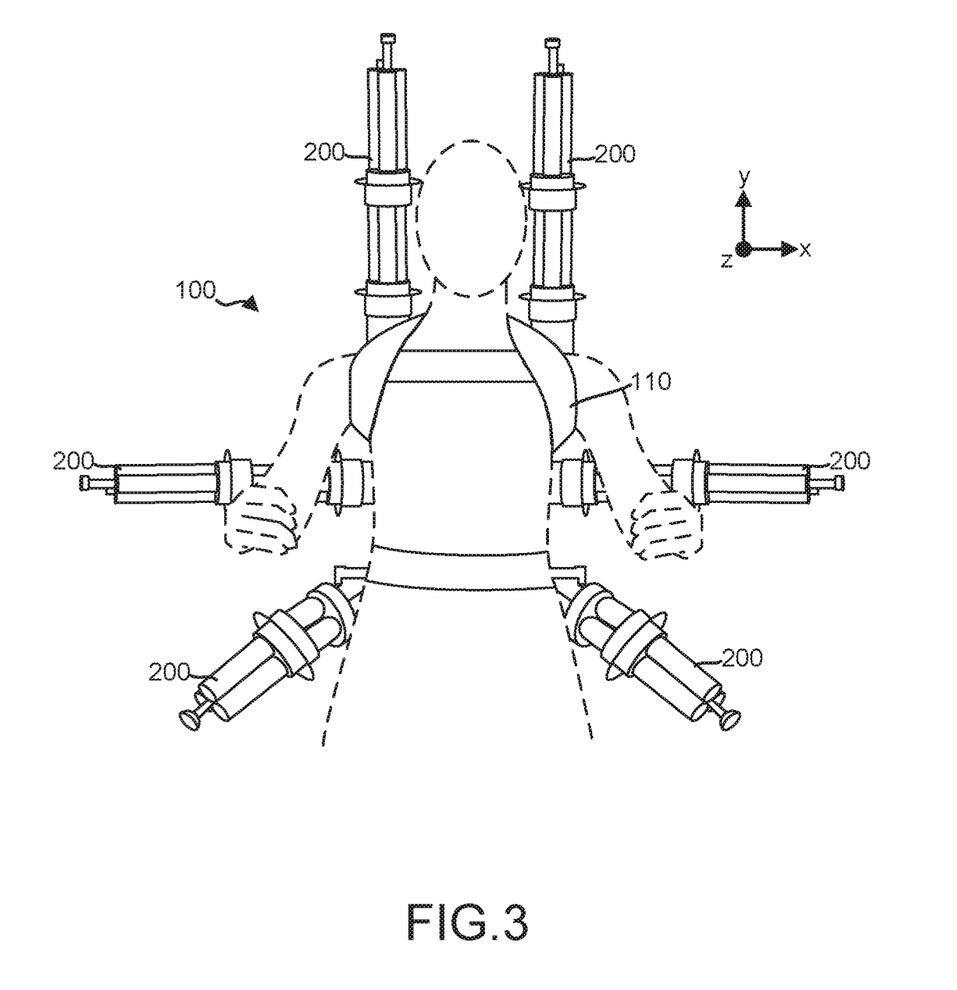
FIG. 3 illustrates various mounting positions of a soft poly-limb in accordance with exemplary embodiments.

Referring now to FIG. 3, various mounting positions of soft poly-limb 200 on soft poly-limb system 100 are illustrated in accordance with various embodiments. Soft poly-limb 200 may be mounted to any suitable portion of backpack mount 110. For example, when viewed from the front (or normal to the x-y plane), soft poly-limb 200 may be mounted to an upper-rear portion of backpack mount 110, middle-rear portion of backpack mount 110, or lower-rear portion of backpack mount 110, wherein rear may refer generally to the negative z-direction. Soft poly-limb 200 may be coupled to a left side or right side of backpack mount 110, wherein left may refer generally to the negative x-direction and right may refer generally to the positive x-direction. While illustrated as being coupled to a rear portion of backpack mount 110 at the discrete locations illustrated in FIG. 3, all suitable mounting locations of soft poly-limb 200 are contemplated herein. Further, soft poly-limb 200 may be detachable in various embodiments such that soft poly-limb 200 may be coupled to a first location on backpack mount 110, decoupled from the first location, and coupled to a second location on backpack mount 110.

Figure 4:
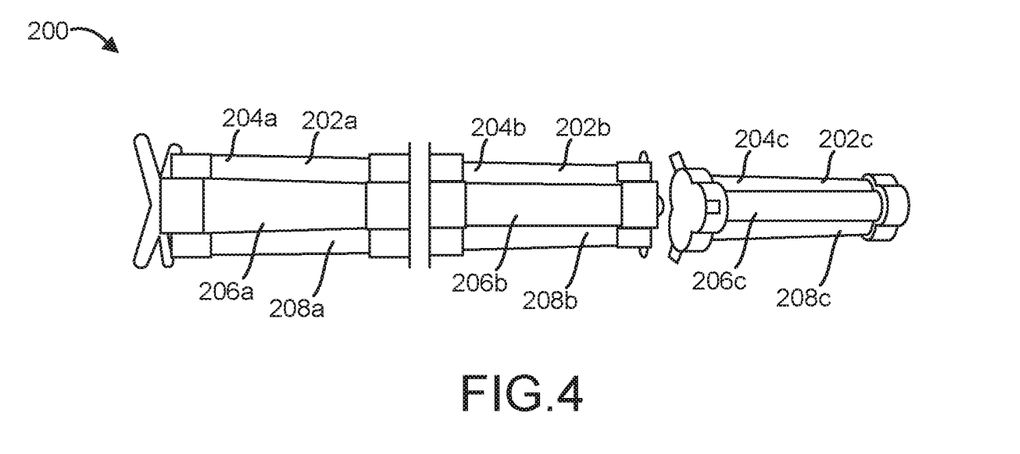
FIG. 4 illustrates a soft poly-limb disassembled into actuator segments in accordance with an exemplary embodiment.

Referring now to FIG. 4, soft poly-limb 200 is illustrated disassembled into three actuator segments 202 in accordance with an exemplary embodiment. In various embodiments, soft poly-limb 200 may be designed to meet one or more functional requirements to better assist a user. For example, in various embodiments, soft poly-limb 200 may comprise a weight of less than 1 kilogram, comprise a maximum diameter of 0.01 meters, be capable of maneuvering a payload of 1 kilogram while fully extended, capable of maneuvering a payload of an object twice the weight of soft poly-limb 200 when not fully extended, comprise a length approximately equal to that of a male arm (0.59 meters), retract to a length half of a fully extended length, having infinite degrees of freedom (DOF), with each actuator segment capable of curving approximately 180 degrees. Other structural and/or functional capabilities in addition to those above are contemplated herein.

In various embodiments, soft poly-limb 200 may comprise at least a first actuator segment 202a, a second actuator segment 202b adjacent to and coupled to first actuator segment 202a, and a third actuator segment 202c adjacent to and coupled to second actuator segment 202b. First actuator segment 202a, second actuator segment 202b, and third actuator segment 202c may be coupled together at axial ends thereof such that the various actuator segments 202 may form a single, elongated soft poly-limb 200, First actuator segment 202a, second actuator segment 202b, and third actuator segment 202c may comprise any suitable material such as a thermoplastic or thermoset material, for example, a thermoplastic polyurethane encased in nylon fabric. The materials of first actuator segment 202a, second actuator segment 202b, and third actuator segment 202c may be any suitable fluidly-sealed material capable of expanding and/or extending in response to applied fluid pressure and returning to a nonexpanded and/or nonextended state in response to removal of applied fluid pressure.

In various embodiments, each actuator segment 202 may comprise a first ring reinforced actuator 204, a second ring reinforced actuator 206, and a third ring reinforced actuator 208. First actuator segment 202a may comprise a first ring reinforced actuator 204a, a second ring reinforced actuator 206a, and third ring reinforced actuator 208a. Similarly, second actuator segment 202b may comprise a first ring reinforced actuator 204b, a second ring reinforced actuator 206b, and a third ring reinforced actuator 208b. Similarly, third actuator segment 202c may comprise a first ring reinforced actuator 204c, a second ring reinforced actuator 206c, and a third ring reinforced actuator 208c. In various embodiments; first actuator segment 202a, second actuator segment 202b, and third actuator segment 202c may comprise more or fewer than three ring reinforced actuators. In various embodiments, the first ring reinforced actuators 204, second ring reinforced actuators 206, and third ring reinforced actuators 208 may be arranged into an equilateral triangle prism; however, they are not limited in this regard and may be arranged in any suitable configuration. The various actuator segments and ring reinforced segments may operate independently or jointly to operate soft poly-limb system 100 as will be discussed further below.

Figure 5A:
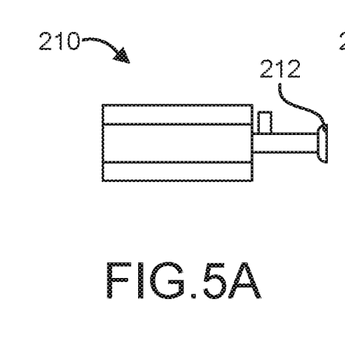
FIG. 5A illustrates a suction cup end-effector for a soft poly-limb system in accordance with an exemplary embodiment.
Figure 5B:
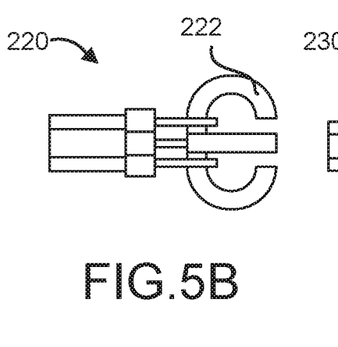
FIG. 5B illustrates a soft grasper end-effector for a soft poly-limb system in accordance with an exemplary embodiment.
Figure 5C:
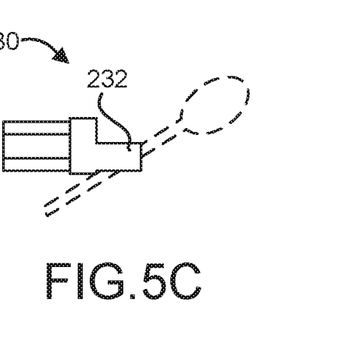
FIG. 5C illustrates a multi-tool holder end-effector for a soft poly-limb system in accordance with an exemplary embodiment.

Referring now to FIGS. 5A-5C, three end-effectors 210, 220, and 230, for use in connection with a soft poly-limb, such as soft poly-limb 200, are illustrated in accordance with an exemplary embodiment. End-effector 210 may comprise a suction cup end-effector, end-effector 220 may comprise a soft grasper end-effector, and end-effector 230 may comprise a multi-tool holder end-effector. A suction cup end-effector such as end-effector 210 may be configured to couple to an object by formation of a vacuum between the distal surface of a suction cup 212 disposed at a distal end of the end-effector 210. A soft grasper end-effector 220 may comprise one or more spring-like members 222 configured to deflect in response to contacting an object and apply a biasing force to the object. In various embodiments, soft grasper end-effector 220 may comprise two, three, four, or any suitable number of spring-like members 222 arranged in any suitable configuration. A multi-tool holder end-effector 230 may comprise any suitable mechanism for applying force to the item to be maneuvered, such as a clamping mechanism 232. The various end-effectors may be selected by a user based on the qualities of the item to be maneuvered by the soft poly-limb and interchangeably coupled to a terminal end of the soft poly-limb. Alternatively, an entire portion of the soft poly-limb may be configured to maneuver a desired object by wrapping around the object.

Figure 6A:
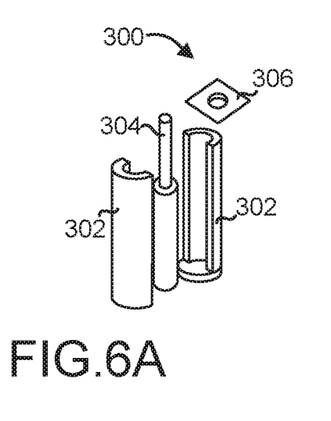
FIG. 6A illustrates a molding process to form an actuator body of a soft poly-limb system in accordance with an exemplary embodiment.
Figure 6B:
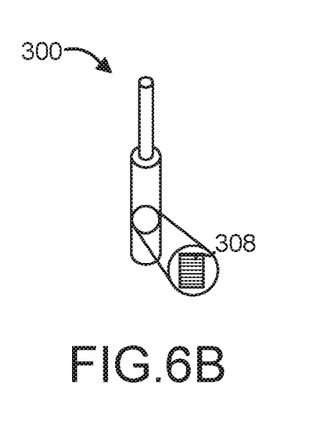
FIG. 6B illustrates a ring-reinforced actuator of a soft poly-limb system in accordance with an exemplary embodiment.
Figure 6C:
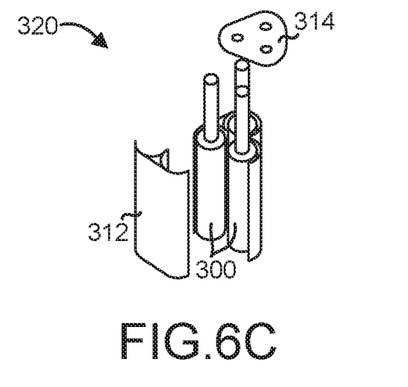
FIG. 6C illustrates a molding process to form an actuator segment of a soft poly-limb system in accordance with an exemplary embodiment.
Figure 6D:
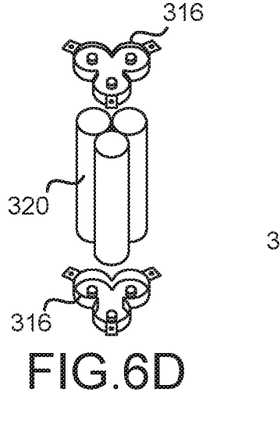
FIG. 6D illustrates an exploded view of modular connector caps coupled to an actuator segment of a soft poly-limb system in accordance with an exemplary embodiment.
Figure 6E:
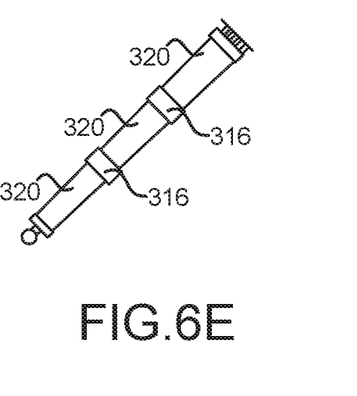
FIG. 6E illustrates a perspective view of an assembled soft poly-limb in accordance with an exemplary embodiment.

Referring now to FIGS. 6A 6E, a soft-poly limb, which may be similar to soft poly-limb 200, is illustrated in various states of assembly, in accordance with various embodiments. FIG. 6A illustrates an exploded view of a molding process of an actuator body 300. In various embodiments, a mold for an actuator body 300 may comprise one or more frame segments 302, a core 304, and a first cap 306. In various embodiments, frame segments 302, core 304, and first cap 306 may be manufactured utilizing any suitable technique, including, for example, additive manufacturing techniques, injection molding, casting, forging, or any other technique. Frame segments 302 may be formed such that one or more segments may be configured to be coupled together to form a mold and contain core 304. As such, frame segments 302 may be coupled together and define an interior space at a radially inner surface and outward of an external geometry of core 304. Frame segments 302 may be manufactured to include one or more protrusions to allow equal spacing of reinforcing rings along a length of the formed ring reinforced actuator. Core 304 may be inserted between frame segments 302 and frame segments 302 may be coupled together to form actuator body 300. First cap 306 may be placed on one or both axial ends to form the mold. Following this, a liquid silicone material may be poured into the mold and cured (for example, by placing the mold in an oven at 60° C. to expedite the curing process), and actuator body 300 may be removed.

Referring to FIG. 6B, a ring reinforced actuator may comprise one or more rings 308 comprising an acrylonitrile butadiene styrene (ABS) or other similar material disposed about actuator body 300. The rings 308 may be manufactured such that each successive ring comprises an incrementally smaller diameter to allow tapering of the reinforced actuator. In various embodiments, the one or more rings 308 which, in various embodiments, may be distributed along an axial length of actuator body 300, may be configured to restrict radial movement of actuator body 300 when actuator body 300 is pressurized. For example, in various embodiment, actuator body 300 may comprise a tubular soft-silicone actuator configured to contain pressurized fluid such as a gas to actuate the soft poly-limb. The soft-silicone actuator may comprise a shore hardness of 30A. However, any suitable hardness may be utilized, as desired. In various embodiments, the one or more rings 308 may be manufactured via any suitable technique and coupled to an external, radially outer surface of actuator body 300. While rings 308 may restrict radial expansion of actuator body 300, rings 308 may also facilitate axial expansion of actuator body 300 as actuator body 300 is pressurized, thereby actuating the soft poly-limb. In various embodiments, the actuator body 300 may comprise any material capable of expanding and retracting in response to fluid pressure at its interior.

With reference to FIG. 6C, multiple ring reinforced actuators 300 may be arranged to form an actuator segment 320. For example, in various embodiments, a two-part mold may be designed to fuse three or more ring reinforced actuators 300 by formation of a silicone sheath around the various ring reinforced actuators. For example, in various embodiments, one or more ring reinforced actuators 300 may be formed in a similar process described with reference to FIG. 6B and arranged in an equilateral triangle prism. The one or more ring reinforced actuators 300 may be enclosed within one or more shell segments 312, which may comprise a silicone material, to form a mold and create a complete actuator segment 320. A second cap 314 comprising a plurality of apertures equal to the number of ring reinforced actuators 300 may be place on one or both axial ends of the ring reinforced actuators to restrict movement of the ring reinforced actuators relative to each other as the molding process is conducted, Each actuator segment 320 may comprise a length of approximately 160 millimeters in various embodiments.

Referring to FIG. 6D, one or more actuator segments 320 may be fitted with modular connector caps 316 on one or both axial ends of actuator segments 320 via a silicone adhesive. For example, in various embodiments, a modular connector cap 316 may comprise a geometry substantially like the axial ends of the actuator segments 320. As illustrated in FIG. 6D, the modular connector caps 316 may comprise three substantially circular portions arranged such that the circular portions may interface with the axial ends of each ring reinforced actuator of the actuator segment 320. Modular connector caps 316 may comprise any suitable lightweight yet rigid material such as a silicone material. Modular connector caps 316 may be configured to provide support for and restrict movement of the ring reinforced actuators and coupled multiple actuator segments together to form a soft poly-limb. A fully assembled exemplary soft poly-limb is illustrated in FIG. 6E.

Figure 7A:
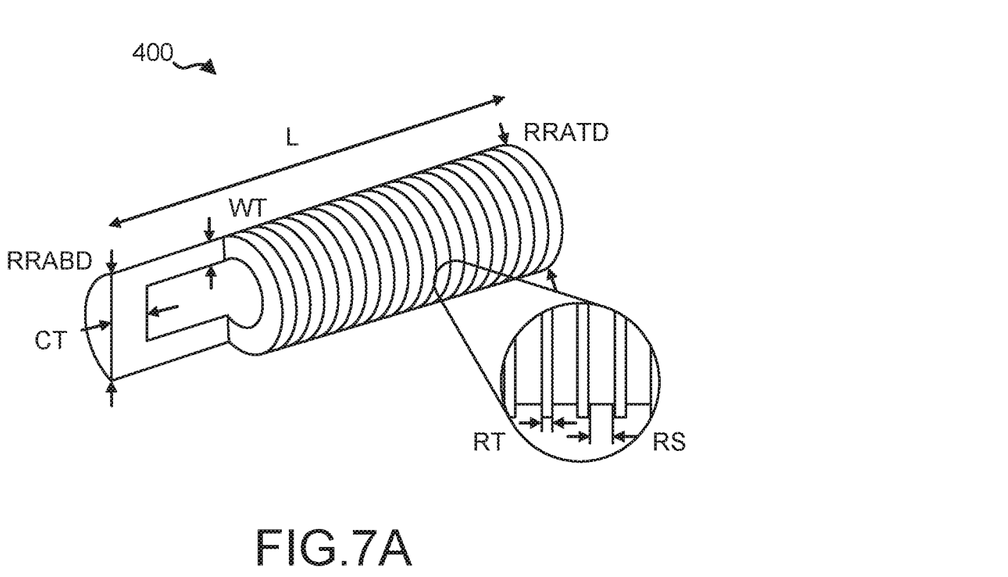
FIG. 7A illustrates various geometrical parameters of a ring-reinforced actuator of a soft poly-limb system in accordance with an exemplary embodiment.
Figure 7B:
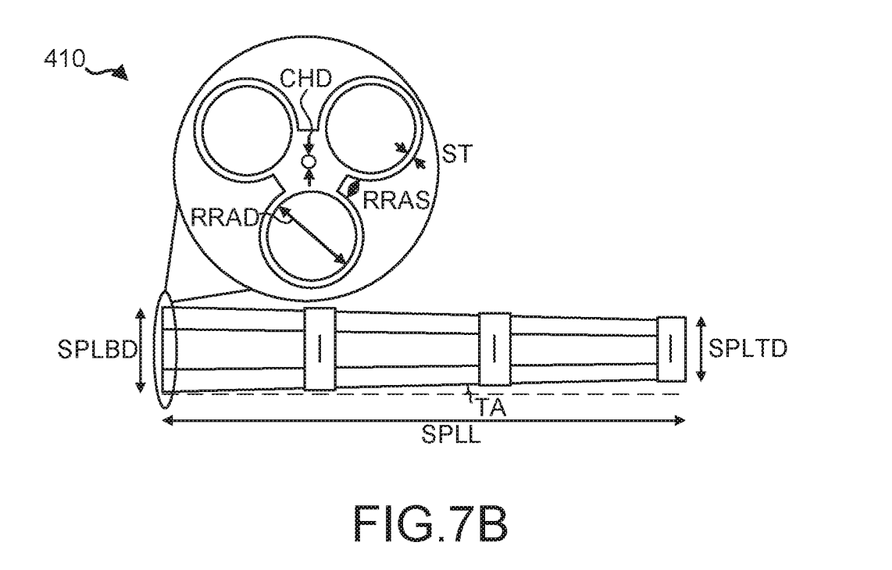
FIG. 7B illustrates various geometrical parameters associated with a soft poly-limb in accordance with an exemplary embodiment.

Referring now to FIGS. 7A and 7B, a ring reinforced actuator 400 and soft poly-limb 410 are illustrated in accordance with exemplary embodiments. As previously stated, varying geometrical parameters of the ring reinforced actuator and soft-poly limb may be determined via experimentally verified finite-element method (FEM) models. Specifically, various geometrical parameters and design variables may be chosen to alter the mechanical properties of the ring reinforced actuator 400 and/or soft poly-limb 410 when ring reinforced actuator 400 and/or soft poly-limb 410 are pressurized. More specifically, with reference to FIG. 7A, ring reinforced actuator 400 may comprise a length (L), a wall thickness (WT), a cap thickness (CT), a ring thickness (RT), a ring spacing (RS), a ring reinforced actuator top diameter (RRATD), and a ring reinforced actuator bottom diameter (RRABD). One or more of the above geometrical parameters or design variables may be selected based on FEM outputs to achieve a desired performance of ring reinforced actuator 400.

Similarly, one or more geometrical parameters and/or design variables associated with soft poly-limb 410 may be selected based on FEM outputs. With reference to FIG. 7B, soft poly-limb 410 may comprise a soft poly-limb length (L) (which in various embodiments may be between 0.5 meters and 0.7 meters), taper angle (TA) (in order to reduce weight at a distal end and bring the soft poly-limb center of gravity closer to a proximal end), soft poly-limb top diameter (SPLTD), soft poly-limb bottom diameter (SPLBD), ring reinforced actuator diameter (RRAD), ring reinforced actuator spacing (RRAS), sheath thickness (ST), and center hole diameter (CHD). One or more of the above geometrical parameters or design variables may be selected based on FEM outputs to achieve a desired performance of soft poly-limb 410.

Figure 8:
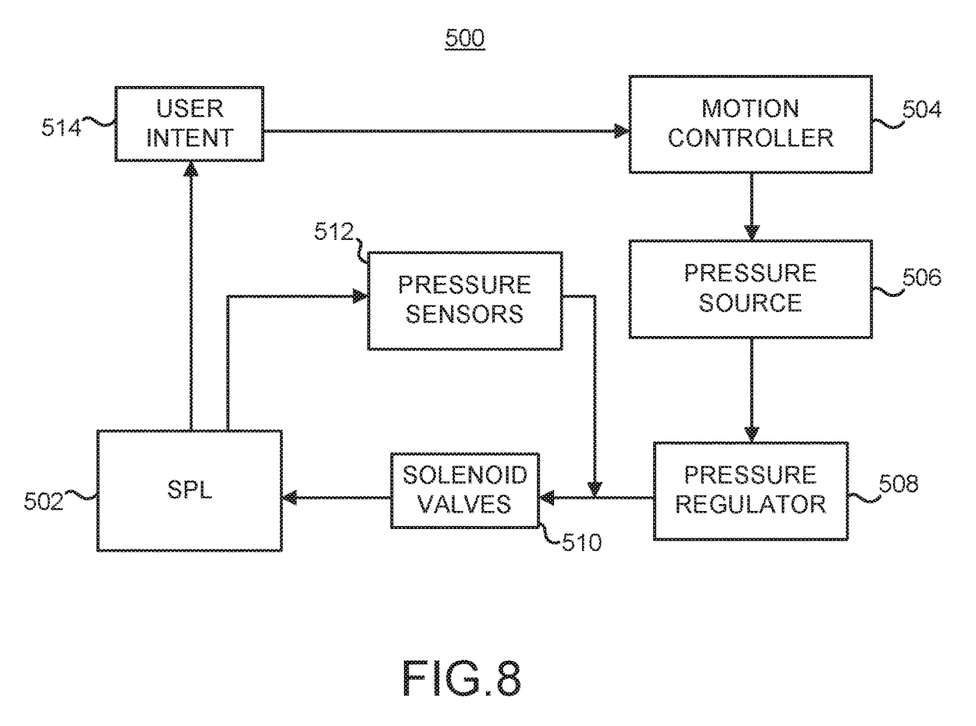
FIG. 8 illustrates a control system flow diagram for a soft poly-limb system in accordance with an exemplary embodiment.

Referring to FIG. 8, a system control flow diagram for a soft poly-limb system 500 is illustrated in accordance with an exemplary embodiment. The system 500 may comprise a soft-poly limb 502 (similar to any of those discussed above), a motion controller 504, a pressure source 506, a pressure regulator 508, at least one solenoid valve 510, and at least one pressure sensor 512. A user's intentions may be illustrated by block 514. In various embodiments, in response to a user desiring to maneuver an object or otherwise operate a soft poly-limb 502, a user may interface with a motion controller 504. Motion controller 504 may comprise a joystick motion controller, an inertial measurement unit motion (IMU) controller, or a surface electromyography (sEMG) motion controller in various embodiments. However, any suitable user input and/or interface components may be utilized, as desired. In various embodiments, a user-desired position of an end-effector coupled to the soft poly-limb 502 may be determined by a discretized motion controller which correlates the position of the motion controller with a pre-set soft poly-limb position. The soft poly-limb 502 may be pneumatically pressured via pressure source 506. Pressure regulator 508, which may comprise a pressure regulator valve or check valve, may regulate a pressure of fluid to the soft poly-limb 502 and one or more solenoid valves 510 may be configured to prevent or allow flow to the soft poly-limb 502. One or more pressure sensors 512 downstream of the pressure regulator 508 and upstream of the one or more solenoid valves 510 may monitor a pressure of various portions of soft poly-limb 502 and be configured to open and/or close the one or more solenoid valves 510 in response to a deficiency or abundance of pressure sensed in soft poly-limb 502 by pressure sensors 512.

Figure 9:
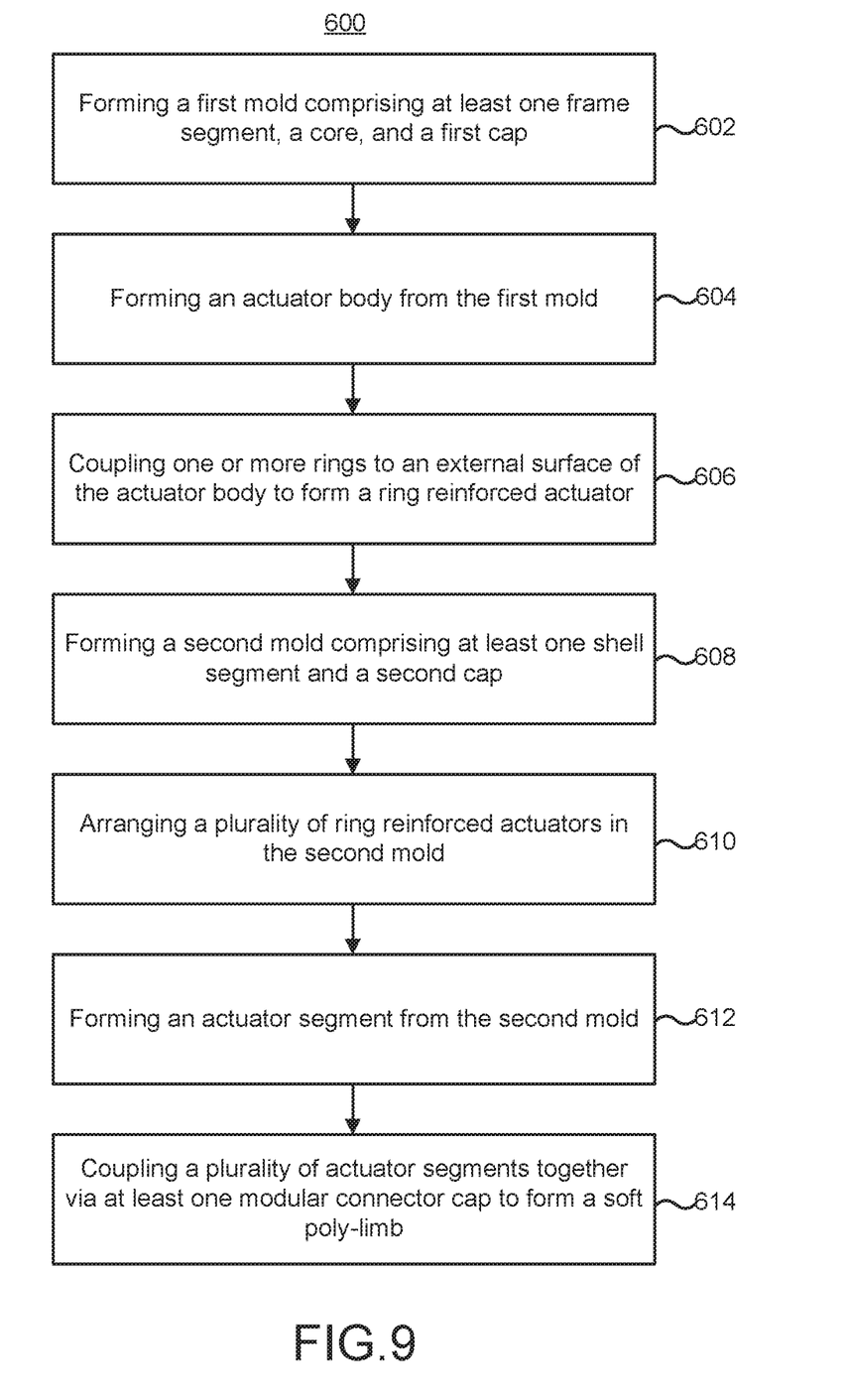
FIG. 9 illustrates a method of manufacturing a soft poly-limb in accordance with an exemplary embodiment.

With reference now to FIG. 9, a method of manufacturing a soft poly-limb 600 is illustrated in accordance with an exemplary embodiment. The method may comprise forming a first mold comprising at least one frame segment, a core, and a first cap (step 602). The method may further comprise forming an actuator body from the first mold (step 604). The method may further comprise coupling one or more rings to an external surface of the actuator body to form a ring reinforced actuator (step 606). The method may further comprise forming a second mold comprising at least one shell segment and a second cap (step 608). The method may further comprise arranging a plurality of ring reinforced actuators in the second mold (step 610), The method may further comprise forming an actuator segment from the second mold (step 612). The method may further comprise coupling a plurality of actuator segments together via at least one modular connector cap to form a soft poly-limb (step 614).

While the principles of this disclosure have been shown in various embodiments, many modifications of structure, arrangements, proportions, the elements, materials and components, used in practice, which are particularly adapted for a specific environment and operating requirements may be used without departing from the principles and scope of this disclosure. These and other changes or modifications are intended to be included within the scope of the present disclosure.

The present disclosure has been described with reference to various embodiments. However, one of ordinary skill in the art appreciates that various modifications and changes can be made without departing from the scope of the present disclosure. Accordingly, the specification is to be regarded in an illustrative rather than a restrictive sense, and all such modifications are intended to be included within the scope of the present disclosure. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, required, or essential feature or element.

As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. Also, as used herein, the terms "coupled," "coupling," or any other variation thereof are intended to cover a physical connection, an electrical connection, a magnetic connection, an optical connection, a communicative connection, a functional connection, and/or any other connection. When language similar to "at least one of A, B, or C" or "at least one of A, B, and C" is used in the specification or claims, the phrase is intended to mean any of the following: (1) at least one of A; (2) at least one of B; (3) at least one of C; (4) at least one of A and at least one of B; (5) at least one of B and at least one of C; (6) at least one of A and at least one of C; or (7) at least one of A, at least one of B, and at least one of C.

What is claimed is:
1. A soft poly-limb system, comprising:
a first actuator segment, a second actuator segment, and a third actuator segment forming the soft poly-limb, wherein each of the first actuator segment, the second actuator segment, and the third actuator segment comprise a plurality of ring reinforced actuators;

a control system whereby a user may control the soft poly-limb;

a backpack mount coupled to the first actuator segment; and a storage pouch coupled to the backpack mount, wherein the first actuator segment, the second actuator segment, and the third actuator segment are storable within the pouch when not in use, wherein each ring reinforced actuator is fluid-driven and comprises a plurality of rings dispersed along an external surface of an actuator body, wherein the plurality of rings are configured to restrain radial expansion and promote linear extension motion, and wherein the soft poly-limb is configured with at least nine degrees of freedom.

2. The system of claim 1, wherein the backpack mount comprises at least two mounting locations for the first actuator segment.

3. The system of claim 2, wherein the plurality of mounting locations comprises an upper-rear right mounting location, an upper-rear left mounting location, a middle-rear right mounting location, a middle-rear left mounting location, a lower-rear right mounting location, and a lower-rear left mounting location.

4. The system of claim 1, wherein each actuator segment is tapered such that the soft poly-limb is tapered.

5. The system of claim 1, wherein each ring reinforced actuator has a first diameter at one end and a second, smaller diameter at a second, opposite end.

6. The system of claim 1, wherein the system is wearable by a user to provide enhanced object manipulation capabilities to the user.

7. The system of claim 1, further comprising an end-effector coupled to the third actuator segment.

8. The system of claim 1, wherein the system comprises at least five actuator segments, or at least seven actuator segments, or at least ten actuator segments.

9. A method of manufacturing a soft poly-limb comprising:

forming an actuator body from a first mold;

coupling one or more rings to the actuator body to form a ring reinforced actuator;

arranging a plurality of ring reinforced actuators in a second mold;

forming an actuator segment from the second mold; and coupling a plurality of actuator segments to form the soft poly-limb.

10. The method of claim 9, wherein coupling a plurality of actuator segments comprises coupling the plurality of actuator segments together via at least one modular connector cap.

11. The method of claim 9, wherein the first mold comprises at least one frame segment, a core, and a first cap.

12. The method of claim 9, wherein arranging the plurality of ring reinforced actuators comprising arranging the plurality of ring reinforced actuators in an equilateral triangle prism.

* * * * *